(12) United States Patent
Bonk

(10) Patent No.: US 12,325,337 B2
(45) Date of Patent: Jun. 10, 2025

(54) OCCUPANT SUPPORT SURFACE HEATER

(71) Applicant: Faurecia Automotive Seating, LLC, Auburn Hills, MI (US)

(72) Inventor: Jeffery T. Bonk, Chesterfield, MI (US)

(73) Assignee: Faurecia Automotive Seating, LLC, Auburn Hills, MI (US)

( * ) Notice: Subject to any disclaimer, the term of this patent is extended or adjusted under 35 U.S.C. 154(b) by 1006 days.

(21) Appl. No.: 17/245,745

(22) Filed: Apr. 30, 2021

(65) Prior Publication Data

US 2022/0348121 A1 Nov. 3, 2022

(51) Int. Cl.
*B60N 2/56* (2006.01)
*A61L 2/04* (2006.01)
*A61L 2/26* (2006.01)
*B60R 16/03* (2006.01)
*B60R 16/037* (2006.01)
(Continued)

(52) U.S. Cl.
CPC ............... *B60N 2/56* (2013.01); *A61L 2/04* (2013.01); *A61L 2/26* (2013.01); *B60R 16/03* (2013.01); *B60R 16/037* (2013.01); *H05B 3/145* (2013.01); *H05B 3/36* (2013.01); *A61L 2202/11* (2013.01); *A61L 2202/25* (2013.01); *H05B 2203/004* (2013.01); *H05B 2203/016* (2013.01); *H05B 2203/017* (2013.01); *H05B 2214/04* (2013.01)

(58) Field of Classification Search
CPC .......... H05B 2214/04; H05B 2203/016; H05B 2203/004; H05B 3/36; H05B 3/14; B60R 16/037; B60R 16/03; A61L 2/26; A61L 2/04; B60N 2/56
USPC .................................................. 219/202, 201
See application file for complete search history.

(56) References Cited

U.S. PATENT DOCUMENTS 4,162,393 A   7/1979   Balboni
6,150,642 A   11/2000  Weiss
(Continued)

FOREIGN PATENT DOCUMENTS

CN   109526077 A   3/2019
DE   29911783 U1   11/2000
(Continued)

OTHER PUBLICATIONS

Office Action dated Mar. 28, 2024 for U.S. Appl. No. 18/213,589, (pp. 1-11).
(Continued)

*Primary Examiner* — Eric S Stapleton
*Assistant Examiner* — Yeong Juen Thong
(74) *Attorney, Agent, or Firm* — Barnes & Thornburg LLP

(57) ABSTRACT

An occupant support surface heater includes a foundation, a cover, an optional comfort layer, an activation layer, and at least one bus bar secured between the foundation and the cover. The foundation may include a foam pad and the comfort layer includes a conductive material mat that is contiguous with the foundation. The activation layer includes thermally conductive material in the form of an inorganic or organic nanotube structure to provide efficient thermal diffusion and heat delivery for the occupant support. The occupant support surface heater may be used to heat an occupant in the occupant support or to provide heat at a predetermined temperature for a predetermined period of time in order to destroy live viruses or live bacteria at a surface of the unoccupied occupant support.

18 Claims, 2 Drawing Sheets

(51) Int. Cl.
*H05B 3/14* (2006.01)
*H05B 3/36* (2006.01)

(56) References Cited

U.S. PATENT DOCUMENTS

| | | | |
|---|---|---|---|
| 8,608,892 B2 | 12/2013 | Winter | |
| 9,191,997 B2 | 11/2015 | Weib | |
| 9,241,373 B2 | 1/2016 | Schaeffer | |
| 9,457,702 B2 | 10/2016 | Tüskes | |
| 10,253,452 B2 | 4/2019 | Hwang | |
| 10,793,033 B2 | 10/2020 | Durkee | |
| 11,370,337 B2 | 6/2022 | Greenwood | |
| 11,719,557 B2 * | 8/2023 | Wilson | G01D 5/2417 324/686 |
| 2001/0052590 A1 * | 12/2001 | Ishida | H01C 7/021 252/500 |
| 2004/0173594 A1 | 9/2004 | Weiss | |
| 2009/0262175 A1 * | 10/2009 | Kim | B41J 2/14129 257/E21.078 |
| 2015/0048658 A1 * | 2/2015 | Gawade | B60N 2/5642 297/180.12 |
| 2015/0239379 A1 * | 8/2015 | Yoshida | A47C 7/748 297/180.12 |
| 2015/0251597 A1 | 9/2015 | Salter | |
| 2019/0208580 A1 * | 7/2019 | Conner | H05B 3/342 |
| 2020/0189428 A1 * | 6/2020 | Kim | B60N 2/75 |
| 2023/0130566 A1 * | 4/2023 | Durfee | H05B 3/34 297/180.12 |
| 2024/0424964 A1 | 12/2024 | Bonk | |
| 2024/0424965 A1 | 12/2024 | Bonk | |
| 2025/0026121 A1 | 1/2025 | Bonk | |

FOREIGN PATENT DOCUMENTS

| | | |
|---|---|---|
| DE | 102007001132 A1 | 7/2008 |
| DE | 102012000445 A1 | 9/2012 |
| DE | 102016110546 A1 | 12/2016 |
| EP | 3892063 A1 | 10/2021 |
| GB | 1287286 A | 8/1972 |
| JP | 05139303 A | 11/1991 |
| JP | 2006213237 A | 8/2006 |
| JP | 4706111 B2 | 6/2011 |
| WO | 200720526 A2 | 4/2007 |
| WO | 202043679 A1 | 3/2020 |
| WO | 2020118117 A1 | 6/2020 |

OTHER PUBLICATIONS

Flexible Coated Conductive Textiles as Ohmic Heaters in Car Seats, by Petru et al., Applied Sciences, vol. 13, 6874, published Jun. 6, 2023 (Year: 2023).
https://leatherseats.com/seat-heater-guide/ (Year: 2022), last accessed on Apr. 3, 2024, 10 pages.
Office Action dated Sep. 4, 2024 for U.S. Appl. No. 18/213,589, (pp. 1-11).

* cited by examiner

OCCUPANT SUPPORT SURFACE HEATER

BACKGROUND

The present disclosure relates to occupant supports, and more specifically to surface heaters in occupant supports.

SUMMARY

According to the present disclosure a surface heater on an occupant support comprises a foundation defining an inner layer of the occupant support and a cover defining an outer layer of the occupant support, an activation layer, and at least one bus bar secured between the foundation and the cover.

In illustrative embodiments, the foundation includes a foam pad and the cover includes at least one of a cloth, vinyl, leather, and faux leather layer.

In illustrative embodiments, a comfort layer is provided between the activation layer and the foundation.

In illustrative embodiments, the comfort layer includes a conductive material mat that is thinner than the foundation layer and the comfort layer is contiguous with the foundation.

In illustrative embodiments, the activation layer includes thermally conductive material in a nanotube structure configured to provide thermal diffusion across the activation layer and subsequently to the comfort layer.

In illustrative embodiments, the nanotube structure includes a carbon nanotube structure configured to reach a predetermined thermal diffusion rate across the activation layer.

In illustrative embodiments, the activation layer includes an inorganic material to provide thermal diffusion across the activation layer and subsequently to the comfort layer.

In illustrative embodiments, the nanotube structure is contiguous with the comfort layer and the cover to enable heat transfer from the nanotube structure across the comfort layer and through the cover.

In illustrative embodiments, the nanotube structure comprises a carbon nanotube film.

In illustrative embodiments, the bus bar further comprises a conductive ink printed onto the activation layer.

In illustrative embodiments, the bus bar comprises one of a screen printed and a silkscreen printed bus bar printed onto the activation layer.

In illustrative embodiments, the bus bar comprises a pair of bus bars on opposing sides of the activation layer.

In illustrative embodiments, each bus bar is tucked into a trench of the foundation under the activation layer and the cover.

In illustrative embodiments, a predetermined temperature is reached for a predetermined period of time for destroying any live virus or bacteria on the opposing surface of the cover with respect to the foundation.

In illustrative embodiments, the nanotube structure comprises an armchair arrangement carbon nanotube film directly under the cover and at an upper surface of the activation layer with respect to the foundation.

In illustrative embodiments, the nanotube structure comprises a zigzag arrangement carbon nanotube film directly under the cover and at an upper surface of the activation layer with respect to the foundation.

In illustrative embodiments, the nanotube structure comprises a chiral arrangement carbon nanotube film directly under the cover and at an upper surface of the activation layer with respect to the foundation.

In illustrative embodiments, a method for assembling a surface heater on an occupant support comprises a foundation defining an inner layer of the occupant support, placing an activation layer above the foundation, and including at least one bus bar contiguous with the activation layer between the foundation and a cover.

In illustrative embodiments, the method comprises placing a comfort layer between the activation layer and the foundation.

In illustrative embodiments, the bus bar is screen-printed or silkscreen printed such that the surface heater is configured to reach a predetermined temperature is reached for a predetermined period of time for destroying any live virus or bacteria on the opposing surface of the cover with respect to the foundation.

Additional features of the present disclosure will become apparent to those skilled in the art upon consideration of illustrative embodiments exemplifying the best mode of carrying out the disclosure as presently perceived.

BRIEF DESCRIPTIONS OF THE DRAWINGS

The detailed description particularly refers to the accompanying figures in which.

DETAILED DESCRIPTION

Figure 1:
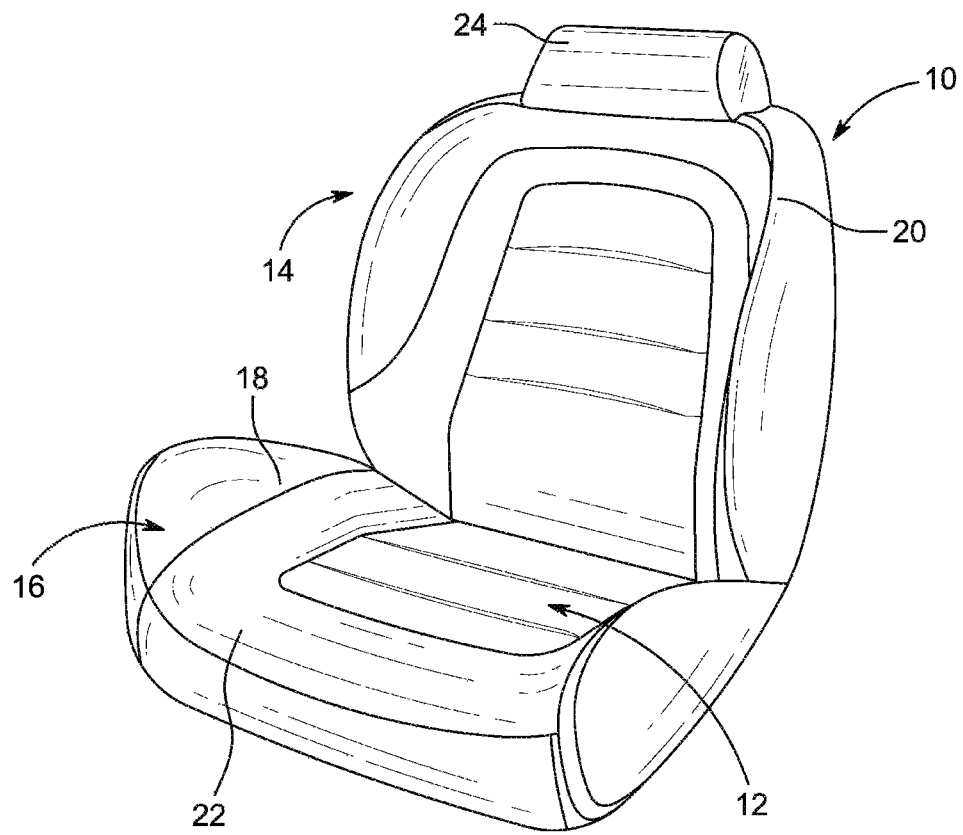
FIG. 1 is a top perspective view of an occupant support with an occupant support surface heater therein.

FIG. 1 shows an occupant support 10 that includes an occupant support surface heater 12. The occupant support 10 has a seat frame (not shown) with a seat back 14 and a seat cushion 16. The seat frame is attached to tracks (not shown), which in turn, are attached to a vehicle (not shown). The occupant support may also include discrete sections, such as a seat cushion side bolster 18, a seat back side bolster 20, an adjustable length cushion 22, and a headrest 24.

Figure 2:
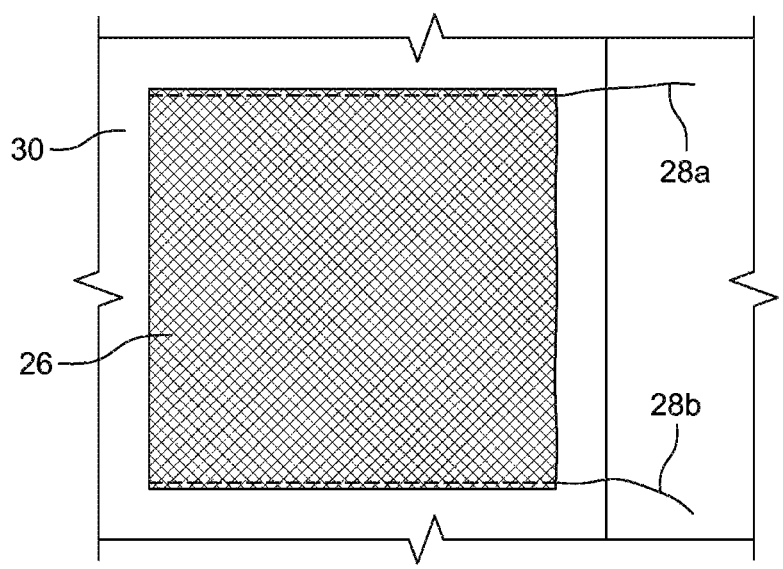
FIG. 2 shows a top plan view of an activation layer with a pair of bus bars integrated therein and extending from the activation layer.

FIG. 2 shows selected portions of the occupant support surface heater 12 in isolation. The activation layer 26 is connected to at least one bus bar 28. A pair of bus bars is illustrated in FIG. 2 as 28a and 28b. A carrier substrate 30 may also be provided as part of the occupant support surface heater 12. The carrier substrate may be comprised of any suitable type of material, such as fabric, vinyl, nylon, or combinations thereof.

Figure 3:
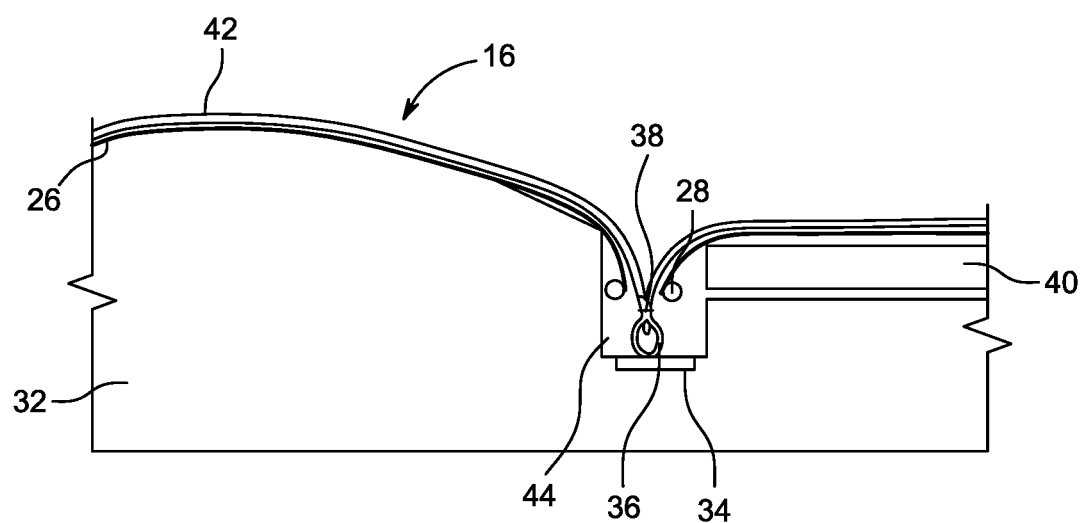
FIG. 3 shows a diagrammatic sectional view of an occupant support surface heater installed on an occupant support.

FIG. 3 shows a diagrammatic sectional view of an occupant support surface heater 12 when installed on the occupant support 10 at the seat cushion 16. Although this example shows the occupant support surface heater 12 installed on the seat cushion 16, it may also be modified to fit in substantially the same way on one or more of the seat cushion side bolster 18, a seat back side bolster 20, an adjustable length cushion 22, and a headrest 24.

A foundation 32 of the occupant support 10 may be vehicle seat foam, which is, for example, polyurethane foam that defines an inner layer. An anchor 34 provides a mounting location for a retainer 36 to connect the outer layer, cover 42 in this example, to the foundation 32, as shown in FIG. 3. The retainer 36 is an intermediate section to hold the occupant support surface heater 12 in place on the occupant support 10. A trench 44 houses the retainer 36 and is substantially closed at the cover 42 with a listing strip 38, as shown in FIG. 3.

The retainer 36 may be any suitable type of mechanical fastener, including but not limited to hog rings, C-shaped retaining fasteners, or other types of crescent rings for securing the cover 42 to the foundation 32. The cover 42 is generally attached to a listing strip 38. The listing strip 38 is connected to retainer 36, which is configured to mount to an anchor 34 within the foundation 32. The anchor 34 may be any suitable mount embedded into or joined with foundation 32, such as a listing seat foam wire or similar stationary anchor, for retainer 34 to attach to.

Once installed in the occupant support 10, the surface heater 12 may be manually or automatically controlled. A mechanical or electrical switch may be used to provide or cut power to the surface heater 12 via at least one bus bar 28. Although FIG. 2 illustrates a pair of bus bars, 28a and 28b, one or several may be used, and the illustration is not limiting. For example, a smaller surface area of the activation layer 26 may be used. The desired results may be achieved with only one bus bar 28. In one embodiment, the pair of bus bars 28a, 28b provide a positive and a negative terminal, respectively, for the surface heater 12.

Likewise, FIG. 3 illustrates another non-limiting example of an occupant support surface heater 12 on a seat cushion 16. The surface heater 12 may come in different shapes, sizes, locations, and layers as is suitable for the application on an occupant support. For example, a surface heater 12 incorporated into an occupant support having an adjustable length cushion 22 may have a different shape of the surface heater 12 with respect to the seat cushion shown in FIG. 3. A few other non-limiting examples of locations that the surface heater 12 could be installed include, but are not limited to, a seat cushion side bolster(s) 18, a seat back side bolster(s) 20, and a headrest 24.

The at least one bus bar 28 may include conductive ink printed onto the activation layer 26. This could be achieved by conductive ink being screen printed or silkscreen printed onto the activation layer 26. The bus bar 28, whether initially applied as ink or not, may include a coating for improving physical durability, electrical conductivity, and/or improved thermal diffusion.

Once electric current travels to the at least one bus bar 28, the activation layer 26 is engaged. The activation layer 26 is made of a suitable material or combination of suitable materials so that the electric flow is resisted while the activation layer 26 remains thermally conductive. Once the flow of electricity is resisted, the activation layer 26 converts the electric current flow from the at least one bus bar 28 into heat. The heat is then diffused through the activation layer 26, for example, by conduction, such that heat energy is spread across the activation layer 26 and is then conducted and radiated from the activation layer 26 to the cover 42. Subsequently, the heat may be transferred to an occupant seated on the occupant support 10, the cabin of the vehicle, and/or the atmosphere outside the occupant support beyond the cover 42 outside of the occupant support 10. This allows the occupant to ease and relax muscles, especially in cold weather, because the surface heater 12 is close in proximity to the occupant's body. This means that the occupant's body warms up faster than an occupant support 10 without the surface heater 12. In another example, this may also mean that the occupant's body warms up faster as compared to heaters which heat air and use air, or only air, as the heat transfer medium to the occupant.

The at least one bus bar 28 includes an electrically conductive material that connects to a power system (not shown), such as a vehicle's power system, to the occupant support 10 for the surface heater 12 to function. The bus bar 28 may be a strip, weave, or line of material that is arranged in a variety of shapes and sizes based on the application of the occupant support 10. As non-limiting examples, a weave of copper wires, a strip of aluminum or aluminum alloy, a cord of brass, or a combination thereof may be used for bus bar 28. A coating may be applied to the bus bar 28 to meet conductivity specifications for the occupant support 10. The shape of the bus bar 28 may be generally flat but it may take different suitable forms based on the location and packaging space required by the occupant support 10.

In some embodiments, the surface heater 12 may include a power monitoring device. The power monitoring device may be configured to set a predetermined power baseline so as to improve heated occupant support efficiency. The power monitoring device may also act as a failsafe in case the temperature of the activation layer reaches an unsafe, or predetermined, temperature for the occupant support 10 or other components of the surface heater 12. In this case, the power monitoring device may act as a switch that cuts or adjusts power to the surface heater 12 when the predetermined temperature is reached.

The cover 42 of the occupant support 10 may provide protection for all components beneath the cover 42 in the occupant support 10 while maintaining a lasting desired outer aesthetic and functionality for the surface heater 12. Natural or synthetic materials may be used for cover 42, including but not limited to cloth of a particular fabric, vinyl, neoprene, animal hide such as leather or sheepskin, mesh, fur, and faux fur. Some cover materials may be more suitable than others in delivering heat via surface heater 12. Accordingly, the specifications of the seat heater 12 may be modified for the desired heat transfer rate and diffusion to occur.

Referring to FIG. 3, the optional comfort layer 40 is included as a sandwiched layer between the foundation layer 32 and the activation layer 26. FIG. 3 depicts spacing between components for illustrative purposes only, but the foundation layer 32, comfort layer 40, activation layer 26, and cover 42 are all substantially contiguous along the entire surface area of comfort layer 40 at the activation layer 26 side. The comfort layer 40 is a pad or sheet that is generally softer with respect to the foundation 32 and generally stiffer than the cover 42.

Trench 44 in the foundation layer 32 is used to fix the comfort layer 40, activation layer 26, and cover 42 against foundation layer 32 in compression. The at least one bus bar 28 is also located in the trench 44 to minimize visual unsightliness. The location of the at least one bus bar 28 also increases packaging efficiency within the occupant support 10 for the surface heater 12.

The activation layer 26 includes electrically resistive and thermally conductive material. The thermally conductive material may include an organic or inorganic material in a nanotube structure. Even inorganic nanotubes behave similarly to carbon nanotubes and may have desirable structural, thermal dispersion, and electrical properties. Carbon nanotube structures are beneficial for their electric conductivity and tensile strength in enabling efficient energy transfer from electricity to heat via the at least one bus bar 28 to the activation layer 26.

Non-limiting examples of materials that may be suitable for activation layer 26 as inorganic nanotube materials include Molybdenum disulfide and Tungsten disulfide. Non-limiting examples of materials that could be suitable for activation layer 26 as organic nanotube materials include carbon nanotubes, which may have any suitable molecular structure. One non-limiting activation layer includes CNT Dispersion PA 422019, manufactured by Battelle at 505 King Avenue, Columbus, Ohio 43201. It is appreciated that some carbon nanotube structures have single-walled and multi-walled structures with different basic structures dependent on how the carbon nanotube graphene sheets are spooled. Carbon nanobuds may also be included if desired, in order to achieve the necessary physical properties along the entire activation layer 26 or some localized portion of the activation layer 26. Different structures have characteristics that may be more suitable in some applications of the surface heater 12 than others.

Surface heater 12 provides the occupant with heat efficiently when an occupant is using occupant support 10. Another purpose of the surface heater 12 may be to sanitize various surfaces of the occupant support 10. Viruses and bacteria may be killed at certain temperatures when the occupant support 10 is not in use by an occupant. As a non-limiting example, a particular virus or bacteria could be killed by the surface heater 12 when a vehicle is locked with no one inside. A temperature of 200 degrees Fahrenheit or higher could be safely reached in about 15 minutes. This surface sanitization process may occur when the vehicle is unoccupied, for example, when a sensor included in the occupant support 10 determines that the occupant support is unoccupied.

The invention claimed is:

1. An occupant support comprises:
   a foundation providing an inner layer of the occupant support;
   a cover providing an outer layer of the occupant support and the cover covers the inner layer of the occupant support; and
   a surface heater including
      an activation layer positioned between the inner layer and the outer layer, the activation layer is formed into a conductive sheet that is configured to provide heat to the cover and
      at least one bus bar arranged between the foundation and the cover and configured to supply power to the activation layer,
   wherein a comfort layer is provided between the activation layer and the foundation,
   wherein the activation layer includes a nanotube structure configured to provide thermal diffusion across the activation layer and to the comfort layer,
   wherein the nanotube structure comprises a carbon nanotube film,
   wherein the at least one bus bar includes a first bus bar arranged between the foundation and the cover and coupled to the carbon nanotube film, and a second bus bar arranged between the foundation and the cover and coupled to the carbon nanotube film such that the carbon nanotube film extends continuously between the first bus bar and the second bus bar, and
   wherein the first bus bar is arranged to extend solely along a first side of the carbon nanotube film and the second bus bar is arranged to extend solely along a second side of the carbon nanotube film opposite the first side, and the first and second bus bars are coupled to a power source to supply power to the nanotube structure by conducting power, in series, from the power source to the first bus bar, through the nanotube structure, and then through the second bus bar.

2. The occupant support of claim 1, wherein the nanotube structure is configured to reach a predetermined thermal diffusion rate across the activation layer.

3. The occupant support of claim 2, wherein the nanotube structure is directly under the cover and provides an upper surface of the activation layer with respect to the foundation.

4. The occupant support of claim 1, wherein the nanotube structure is contiguous with the comfort layer and the cover to enable heat transfer from the nanotube structure across the comfort layer and through the cover.

5. The occupant support of claim 1,
   wherein at least one of the first bus bar and the second bus bar is located within a trench formed in the foundation.

6. The occupant support of claim 5, wherein the at least one of the first bus bar and the second bus bar located in the trench is positioned below an upper surface of the comfort layer.

7. The occupant support of claim 5, further comprising: a listing strip coupled to the cover, a retainer coupled to the listing strip, and an anchor located within the foundation and configured to mount with the retainer in the trench to couple the cover with the foundation.

8. An occupant support comprises:
   a foundation providing an inner layer of the occupant support;
   a cover configured to overlie the foundation to provide an outer layer of the occupant support; and
   a surface heater including:
      an activation layer positioned between the inner layer and the outer layer, the activation layer is formed into a conductive sheet that is configured to provide heat to the cover and
      at least one bus bar arranged between the foundation and the cover and configured to supply power to the activation layer,
   wherein a comfort layer is provided between the activation layer and the foundation,
   wherein the activation layer includes a nanotube structure configured to provide thermal diffusion across the activation layer,
   wherein the activation layer includes an inorganic material to provide thermal diffusion across the activation layer and subsequently to the comfort layer,
   wherein the at least one bus bar includes a first bus bar arranged between the foundation and the cover and coupled to the nanotube structure, and a second bus bar arranged between the foundation and the cover and coupled to the nanotube structure such that the nanotube structure extends between and interconnects the first bus bar and the second bus bar, and
   wherein at least one of the first bus bar and the second bus bar is located within a trench formed in the foundation to reside beneath an upper surface of the foundation and between the foundation and the cover.

9. The occupant support of claim 8,
   wherein the first bus bar is arranged to extend solely along a first side of the nanotube structure and the second bus bar is arranged to extend solely along a second side of the nanotube structure opposite the first side, and the first and second bus bars are coupled to a power source to supply power to the nanotube structure by conducting power from the power source to the first bus bar, through the nanotube structure, and then through the second bus bar.

10. The occupant support of claim 8, wherein the at least one of the first bus bar and the second bus bar located in the trench is positioned below an upper surface of the comfort layer.

11. An occupant support comprising:
a seat bottom and a seat back, wherein at least one of the seat bottom and the seat back includes a seat cushion providing an inner layer of the occupant support and a cover providing an outer layer of the occupant support and the cover covers the seat cushion of the occupant support; and
a surface heater including an activation layer positioned between the seat cushion and the cover, the activation layer is formed into a conductive sheet that is configured to provide heat to the cover, a first bus bar arranged between the seat cushion and the cover and coupled to the activation layer, and a second bus bar arranged between the seat cushion and the cover and coupled to the activation layer,
wherein the activation layer includes a nanotube structure configured to provide thermal diffusion across the activation layer,
wherein the first bus bar is arranged to extend along a first side of the nanotube structure and the second bus bar is arranged to extend along a second side of the nanotube structure opposite the first side, and the first and second bus bars are coupled to a power source to supply power to the nanotube structure by conducting power from the power source to the first bus bar, through the nanotube structure, and then through the second bus bar, and
wherein at least one of the first bus bar and the second bus bar is located within a trench formed in the seat cushion.

12. The occupant support of claim 11, further comprising a comfort layer located between the activation layer and the seat cushion, and wherein the at least one of the first bus bar and the second bus bar located in the trench is positioned below an upper surface of the comfort layer.

13. The occupant support of claim 11, wherein the activation layer includes an inorganic material to provide thermal diffusion across the activation layer and subsequently to the comfort layer.

14. The occupant support of claim 11, wherein the nanotube structure comprises a carbon nanotube film extending continuously between the first bus bar and the second bus bar.

15. The occupant support of claim 11, wherein the activation layer further includes a carrier substrate layer located between the nanotube structure and the comfort layer.

16. The occupant support of claim 11, wherein the at least one of the first bus bar and the second bus bar extends longitudinally within the trench and is entirely below an upper surface of the seat cushion.

17. The occupant support of claim 11, further comprising: a listing strip coupled to the cover, a retainer coupled to the listing strip, and an anchor located within the trench formed in the seat cushion and configured to engage with the retainer in the trench and adjacent to the at least one of the first bus bar and the second bus bar.

18. The Occupant support of claim 11, wherein the first bus bar is arranged to extend solely along the first side of the nanotube structure and the second bus bar is arranged to extend solely along the second side of the nanotube structure opposite the first side, and the nanotube structure extends continuously between the first bus bar and the second bus bar along an entire length of the nanotube structure.

* * * * *